（12） United States Patent
Loeb (10) Patent No.: US 7,359,601 B2
(45) Date of Patent: Apr. 15, 2008

(54) DEVICE AND METHOD FOR DELIVERY OF LONG WAVELENGTH LASER ENERGY TO A TISSUE SITE

(75) Inventor: Marvin P. Loeb, Huntington Beach, CA (US)

(73) Assignee: Trimedyne, Inc., Lake Forest, CA (US)

(*) Notice: Subject to any disclaimer, the term of this patent is extended or adjusted under 35 U.S.C. 154(b) by 224 days.

(21) Appl. No.: 10/539,893

(22) PCT Filed: Dec. 19, 2003

(86) PCT No.: PCT/US03/41095

§ 371 (c)(1),
(2), (4) Date: Jun. 17, 2005

(87) PCT Pub. No.: WO2004/058328

PCT Pub. Date: Jul. 15, 2004

(65) Prior Publication Data

US 2006/0078265 A1    Apr. 13, 2006

Related U.S. Application Data

(63) Continuation-in-part of application No. 10/324,897, filed on Dec. 20, 2002, now Pat. No. 6,953,458.

(51) Int. Cl.
*G02B 6/06* (2006.01)
*A61B 18/18* (2006.01)
*A61B 1/00* (2006.01)
*A61N 5/06* (2006.01)
*A61N 1/30* (2006.01)

(52) U.S. Cl. ............ 385/117; 385/116; 606/15; 606/3; 606/20; 606/78; 607/88; 607/89; 607/92; 607/104; 604/20; 604/21; 604/26; 604/129; 600/101; 600/105; 600/108

(58) Field of Classification Search ............ 385/117, 385/123, 125, 126, 127, 115, 116, 12; 606/3, 606/13–16, 20–26, 78; 128/898; 607/88–92; 604/20, 26, 27, 28, 544; 600/101, 105, 108, 600/129, 130, 156, 176
See application file for complete search history.

(56) References Cited

U.S. PATENT DOCUMENTS 5,352,221 A * 10/1994 Fumich ............ 606/15

(Continued)

*Primary Examiner*—Brian M. Healy
(74) *Attorney, Agent, or Firm*—Olson & Cepuritis, Ltd.

(57) ABSTRACT

A laser energy delivery device is provided that is suitable for irradiating a body tissue with relatively long wavelength laser energy in the presence of an aqueous liquid without significant absorption of the laser energy by the liquid. The device includes an elongate hollow sheath that has an open aperture at its distal end portion and closed at its proximal end, a laser energy conduit such as an optical fiber or hollow wave guide, within the sheath, the distal end of the conduit being disposed near the open aperture at the distal end portion of the sheath, and the proximal end of the conduit being adapted for connection to a source of long wavelength laser energy. The sheath also includes an inlet port, spaced from the proximal end of the sheath, and adapted to receive and deliver a biologically compatible gas through the sheath to a body tissue site in contact with the open distal end of the sheath. In use, the open aperture at the distal end portion of the sheath is positioned in contact with a body tissue site. Gas, such as carbon dioxide, infused through the sheath displaces an aqueous liquid from the region between the distal end portion of the sheath and the tissue. Laser energy emitted from the distal end portion of the conduit passes through the substantially liquid-free region at the distal end of the sheath and impinges on the tissue to be irradiated. The laser energy can be used to ablate, vaporize, coagulate or shrink tissue at the target zone without interference from aqueous liquids, which tend to absorb relatively large amounts of long wavelength laser energy and reduce the efficiency of tissue ablation.

36 Claims, 5 Drawing Sheets

U.S. PATENT DOCUMENTS

| | | | |
|---|---|---|---|
| 5,470,330 A * | 11/1995 | Goldenberg et al. | 606/7 |
| 6,182,666 B1 * | 2/2001 | Dobak, III | 128/898 |
| 6,451,012 B2 * | 9/2002 | Dobak, III | 606/24 |
| 6,953,458 B2 * | 10/2005 | Loeb | 606/15 |
| 2004/0120668 A1 * | 6/2004 | Loeb | 385/117 |

* cited by examiner

DEVICE AND METHOD FOR DELIVERY OF LONG WAVELENGTH LASER ENERGY TO A TISSUE SITE

CROSS-REFERENCE TO RELATED APPLICATION

This application is a continuation-in-part of U.S. patent application Ser. No. 10/324,897, now U.S. Pat. No. 6,953,458, filed on Dec. 20, 2002.

FIELD OF THE INVENTION

The present invention relates to laser energy delivery devices and their method of use in an aqueous environment. More particularly, the invention relates to laser energy delivery devices useful for delivering laser energy at wavelengths of about 1,300 to 11,000 nanometers, to a body tissue site with reduced interference from surrounding aqueous fluid media.

BACKGROUND OF THE INVENTION

Lasers that emit light energy at wavelengths in the range of about 1,300 to about 11,000 nanometers (long wavelength or "LW" laser energy) are excellent vaporizers of tissue, since their energy is highly absorbed by water, a major constituent of mammalian tissue. When exposed to such long wavelength laser energy, the water in the tissue is rapidly heated and converted to steam, causing ablation or vaporization of the tissue. These properties make long wavelength lasers particularly useful for nonsurgical removal or reduction of tissue.

Typically, laser energy is delivered to a tissue site via an optical fiber or an optical wave guide device adapted for transmission of long wavelength laser energy. The emitting end of the fiber optic or wave guide is placed in close proximity to the desired tissue site. An endoscope is first positioned inside a duct, body cavity, hollow organ or surgically created passageway at the tissue site. The energy emitting end of the optical fiber or wave guide is then threaded through a channel in the endoscope to place the emitting end of the optical fiber or wave guide in the optical position near the tissue. Typically a fiber optic viewing device is also positioned at the working end of the endoscope to view the tissue site as it is being irradiated with laser light energy and to verify the correct positioning of the emitted laser energy.

However, when water, saline, or other aqueous liquid is infused through the endoscope to provide a clear field of view of the tissue inside a duct, body cavity, hollow organ, or surgically created passageway, via the fiber optical viewing device, a substantial amount of the laser energy is wasted. The aqueous liquid between the distal end of the optical fiber and the target tissue absorbs a substantial part of the light energy and creates a steam bubble, which acts as an "optical cavity." The remainder of the laser energy passes through the steam bubble and vaporizes or ablates the target tissue. However, as the steam bubble collapses between pulses of laser energy, liquid flows back into the space between the distal end of the optical fiber and the target tissue, requiring some of the laser energy to again be consumed in recreating the steam bubble between the optical fiber and the tissue, diminishing the amount of laser energy reaching the target tissue.

The above phenomenon was first described by Jeffrey M. Isner et al. in "Mechanism of laser ablation in an absorbing fluid field," *Lasers Surg. Med.* 1988;8(6):543-54, and is commonly referred to as the "Moses Effect" or "parting the water."

Holmium lasers emitting long wavelength light were used in the mid to late 1990's to resect prostate tissue, as described above. However, while the procedure produced benefits comparable to a trans-urethral resection of the prostrate or "TURP" procedure, in which a wire loop is heated by radiofrequency ("RF") energy to cut-out swaths of prostate tissue, the laser procedure typically took about 45 minutes to an hour for a small (20-30 gram prostate) and longer than an hour for larger prostates. As a result, the laser procedure never became popular and is presently used only infrequently.

It would be desirable to enable a substantially greater amount of light energy from long wavelength lasers to be used in an aqueous liquid environment to vaporize tissue without significant quantities of energy being wasted by vaporizing the intervening aqueous liquid.

SUMMARY OF THE INVENTION

A laser energy delivery device of the present invention comprises an elongate hollow sheath having an open aperture at distal end portion thereof and a closed proximal end. The sheath defines a lumen, a gas inlet port and a gas outlet port that serves as the open aperture. The open aperture can be substantially coaxial with a laser energy conduit within the sheath or offset from the longitudinal axis therefrom. The gas inlet port is spaced from the closed proximal end of the sheath and is in open communication with the lumen. The gas inlet port is adapted for connection to a source of a biocompatible gas such as air, argon, carbon dioxide, helium, nitrogen, and the like, or a combination thereof.

A laser energy conduit, such as an optical fiber or an optical wave guide is disposed within the lumen of the sheath. The proximal end of the conduit extends through the closed proximal end of the sheath. The proximal end of the laser energy conduit is adapted for connection to a source of a relatively long wavelength laser energy, i.e., at least about 1,300 nanometers and up to about 11,000 nanometers. The distal end of the laser energy conduit is positioned within the lumen of the sheath near the open aperture. The distal end portion of the energy conduit is adapted to emit laser energy.

The laser energy delivery device can also include a handpiece at the proximal end of the sheath to facilitate handling and placement of the sheath and energy conduit. The gas inlet port can be spaced from the handpiece or can be defined by the handpiece itself.

The distal end of the sheath can be flared out in a bell or funnel-like shape, and can be beveled if desired. The distal end of the sheath, and its accompanying energy conduit, can be bent at an angle from the axis of the handpiece to facilitate placement of the open distal end of the sheath against the tissue that is to be irradiated by laser energy. The laser energy delivery device of the present invention is suitable for delivering relatively long wavelength laser energy to a tissue in an aqueous medium with minimal loss of laser energy to the medium.

When an aqueous liquid is present at the tissue site, carbon dioxide or other biocompatible gas is infused into the sheath or handpiece and through the passageway defined between the optical fiber and the sheath, and displaces the liquid in the region between the distal end of the sheath and the adjacent tissue, creating a substantially liquid-free region between the distal end of the energy conduit, from which laser energy is emitted, and the tissue. The substantially liquid-free region enables a substantially greater portion of the laser energy to be utilized to vaporize the target tissue compared with irradiation through an aqueous liquid that necessarily absorbs and dissipates at least some of the laser energy.

DETAILED DESCRIPTION OF PREFERRED EMBODIMENTS

While this invention is susceptible of embodiment in many different forms, there are shown in the drawings and are described in detail herein specific embodiments of the invention, with the understanding that the present disclosure is an exemplification of the principles of the invention and is not limited to the specific embodiments illustrated.

In the device and method of present invention, air or another biologically compatible gas, such as argon, carbon dioxide, helium, nitrogen, or a mixture thereof, preferably carbon dioxide, is infused into a sheath disposed over a laser energy conduit such as an optical fiber or optical wave guide, and displaces liquid at the distal end of the sheath. Light energy from a laser that is optically coupled to the laser energy conduit is emitted at a wavelength of at least about 1,300 nanometers (referred to herein as long wavelength laser energy, or LW laser energy) from the distal end of the laser energy conduit. The entire sheath has an inside diameter slightly larger than the outside diameter of the optical fiber or wave guide. Preferably, the distal end portion of the sheath has an inside diameter somewhat larger than the inside diameter of the body of the sheath. In a particularly preferred embodiment, the distal end portion of the sheath is flared outwardly into a funnel or bell-like shape. Preferably the LW laser energy has a wavelength in the range of about 1,300 nanometers to about 11,000 nanometers.

When the laser energy delivery device of the present invention is used to vaporize tissue in a duct, hollow organ, body cavity, or surgically created passageway, which is filled with a biologically compatible, clear aqueous liquid, the distal end of the sheath is brought into contact with, or close to, the target tissue. A biologically compatible gas is infused through the sheath to displace the liquid between the distal end of the optical fiber and the target tissue, creating a gas bubble therebetween. As a consequence, the target tissue is vaporized, ablated, or cut without wasting the laser energy by vaporizing the aqueous liquid.

Figure 1:
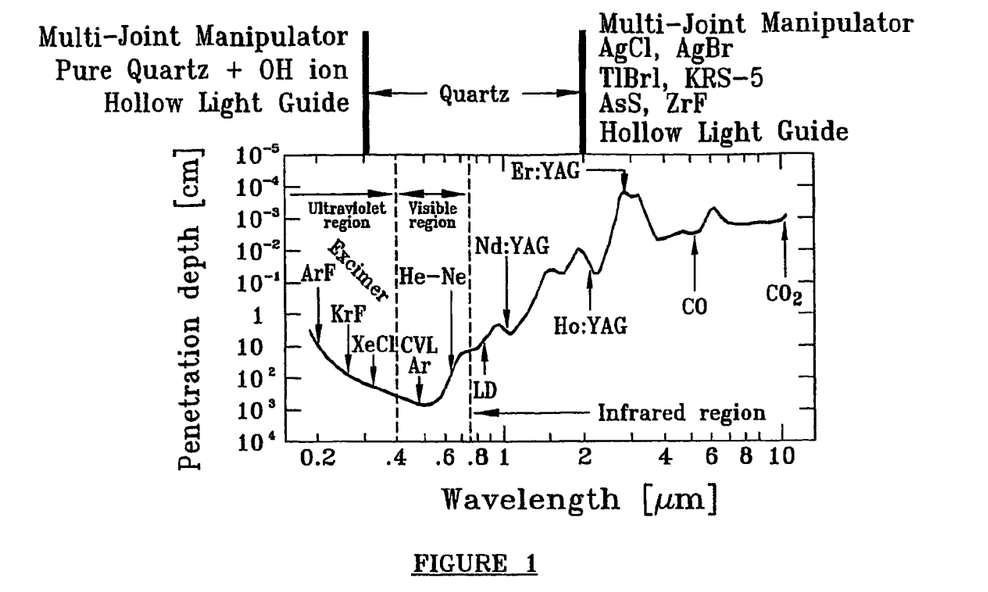
FIG. 1 is a chart showing the relative absorption in water of various wavelengths of light energy.

FIG. 1 illustrates the relative absorption of various wavelengths of light energy in water, according to Y. Hashishin and U. Kubo in "Development of Laser Endoscope for Coagulation and Incision," published in *Lasers in the Musculoskeletal System,* Pg. 81-84, Springer Verlag Berlin (2001). As FIG. 1 shows, light energy from Holmium:YAG, Erbium:YAG, CO, and $CO_2$ lasers is highly absorbed by water.

Figure 2:
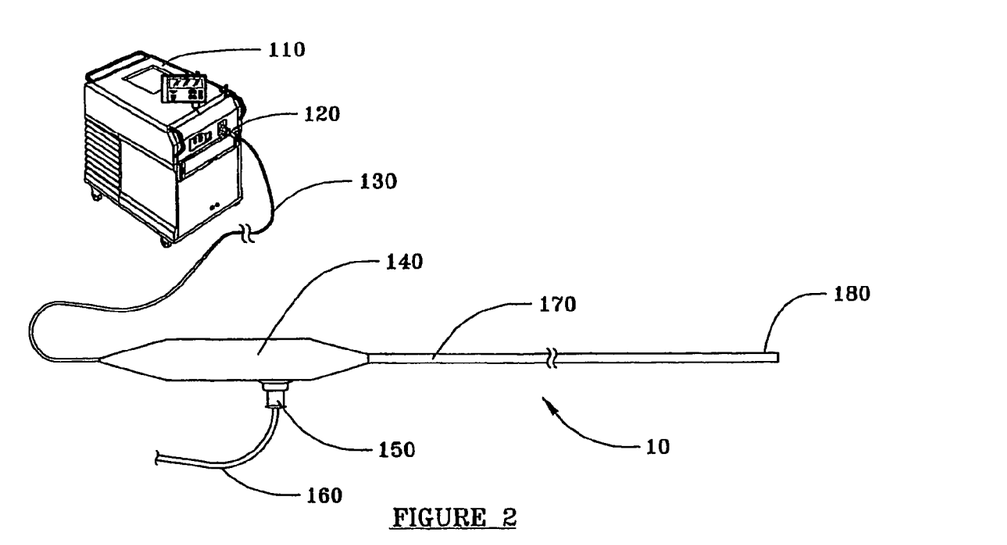
FIG. 2 is an external view of an embodiment of the laser energy delivery device of the present invention.

FIG. 2 illustrates a laser energy delivery system, which includes a LW laser energy source 110, capable of providing continuous wave, gated, or pulsed laser energy at a wavelength in the range of about 1,300 to about 11,000 nanometers, and which is optically connected to a preferred long wavelength laser energy delivery device 10 of the present invention. Laser energy conduit 130 extends through handpiece 140, which is provided to facilitate the handling of laser energy conduit 130. The proximal end of laser energy conduit 130 includes a coupler 120, adapted for connection to a long wavelength laser energy source 110. Handpiece 140 includes luer lock 150, which is in open communication with handpiece 140 and gas supply tube 160. Gas supply tube 160 is removably attached to luer lock 150, and allows transport of air or other biologically compatible gas from a supply source (not shown) into handpiece 140. Sheath 170 extends from within the distal end of handpiece 140 and defines a lumen through which laser energy conduit 130 extends. The distal end portion 180, of sheath 170, is open and allows gas that is infused into sheath 170 through luer lock 150 to exit sheath 170 at its open distal end.

Sheath 170 can be made of any biologically compatible rigid or semi-rigid material. Preferably, sheath 170 is made of stainless steel, a rigid or semi-rigid plastic material, or a flexible, shape-memory nickel-titanium alloy such as nitinol, available from Memry, Inc., Bethel, Conn. Suitable semi-rigid plastic materials include polyvinyl chloride, block polyether amides, and the like materials. Distal end portion 180 of sheath 170 can be made of the same material as sheath 170 or a different material such as a natural or synthetic rubber material or a soft plastic material to facilitate safe contact with biological tissue. Alternatively, distal end portion 180 of sheath 170 can be coated with a natural or synthetic rubber.

Figure 3:
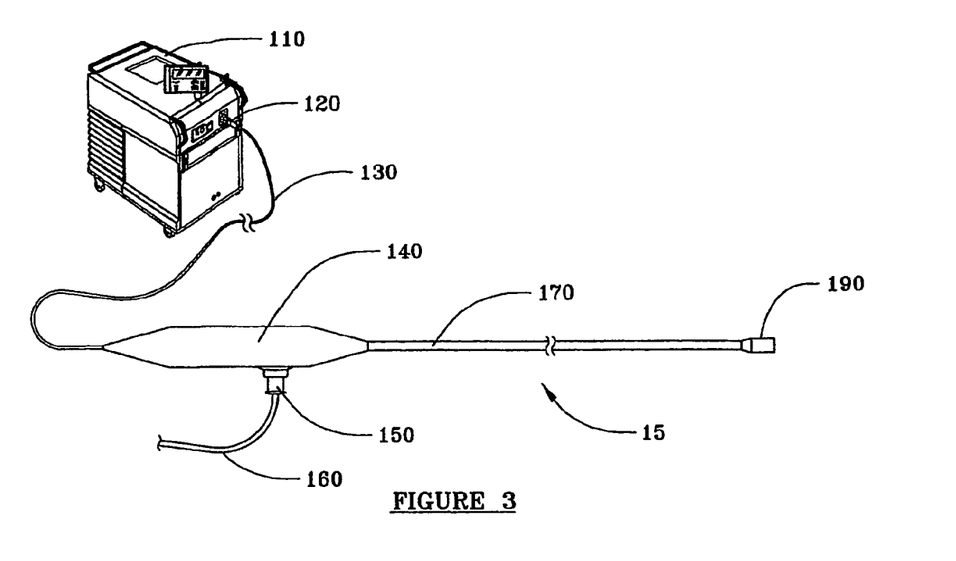
FIG. 3 is an external view of an alternative embodiment of the device of FIG. 2.

FIG. 3 illustrates a preferred embodiment of the present invention. In device 15, the distal end portion consists of an outwardly flared distal end portion 190, instead of being cylindrical as shown in FIG. 2. Flared distal end portion 190 can be a continuation of sheath 170 or can be a separate piece that is fixedly attached to the distal end of sheath 170. Sheath 170 and its flared distal end portion 190 can be made of the same or different materials as described for the embodiment depicted in FIG. 2.

Figure 4:
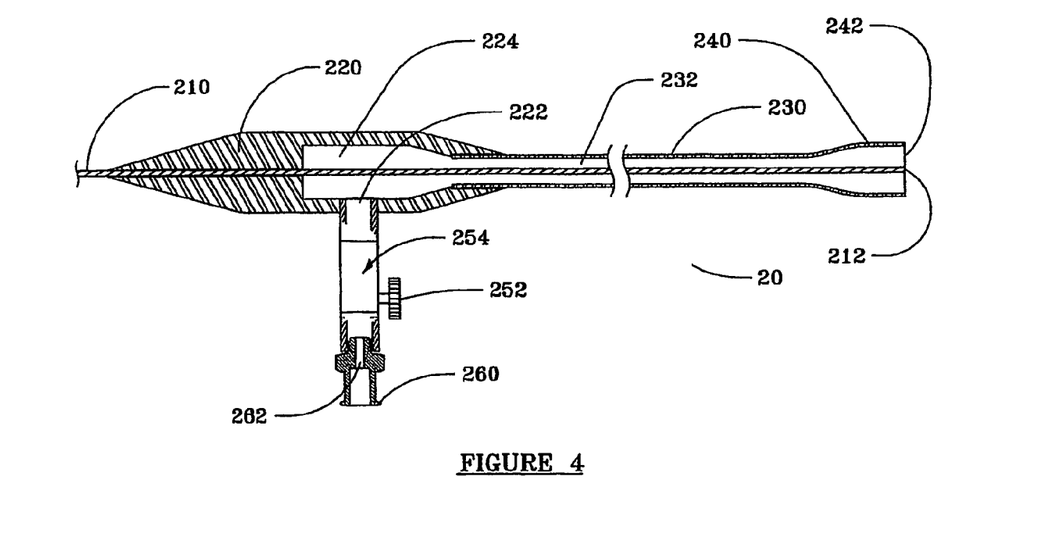
FIG. 4 is a partial, cross-sectional view of the distal end portion of an embodiment of the device of FIG. 3.

FIG. 4 is a partial, cross-sectional view of another preferred embodiment of the LW laser energy delivery device of the present invention. Device 20 includes a handpiece 220, defining port 222 and chamber 224, and a sheath 230. Sheath 230 is fixedly attached to the distal end of handpiece 220 and defines a lumen 232 which is in open communication with chamber 224. Sheath 230 includes a distal end portion 240, which has a larger inside diameter than the inside diameter of the remaining portion of sheath 230. Laser energy conduit 210 extends through handpiece 220, chamber 224 and lumen 232. The distal end 212 of laser energy conduit 210 is positioned approximately at the open distal end 242 of sheath 230. The laser energy conduit 210 is adapted at its proximal end for connection to a LW laser energy source (not shown). Laser energy conduit 210 forms a liquid and gas-tight seal with the handpiece 220 in the region 226 where the conduit 210 extends into the chamber 224.

Needle valve 254 is sealably attached to port 222 of handpiece 220. Knob 252 is operably attached to needle valve 254 such that turning knob 252 in a clockwise direction, for example, seals the needle valve 254 in a closed position. Subsequently, turning knob 252 in a counterclockwise manner moves needle valve 254 to an open position. Luer lock 260 defines channel 262 and is joined to the proximal end of the needle valve 254. When needle valve 254 is in the open position, channel 262 of luer lock 260 is in open communication with port 222 and chamber 224 of handpiece 220 and with lumen 232 of sheath 230.

Figure 5:
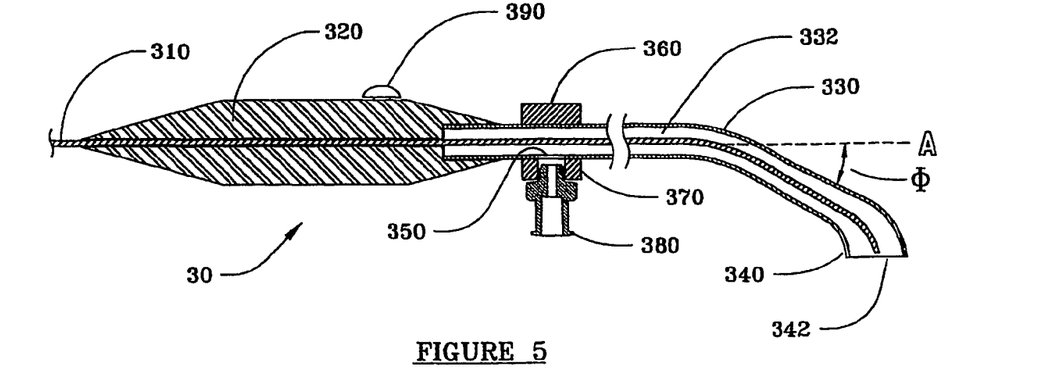
FIG. 5 is a partial cross-sectional view of a preferred embodiment of the device of the present invention.

FIG. 5 illustrates a particularly preferred embodiment of the present invention. Laser energy conduit 310 in device 30 extends through handpiece 320 and is fixedly attached thereto. Sheath 330 extends into handpiece 320 and is attached to handpiece 320 by an adhesive or like expedient. Sheath 330 is bent at an angle φ from axis A of handpiece 320. Sheath 330 can be made, for example, from stainless steel, a rigid or semi-rigid plastic, or a shape-memory nickel-titanium alloy, such as nitinol, or a combination of any of these materials.

When sheath 330 is made of stainless steel, the angle φ at which the sheath 330 can be bent is limited by the relative outside diameter of sheath 330 and the inside diameter of an endoscope through which sheath 330 will be positioned when the device 30 is used. When sheath 330 is made of a flexible, shape-memory alloy, or a flexible or semi-rigid plastic, bend angle φ of sheath 330 can be in the range of about 20° to about 120° from axis A, preferably in the range of about 30° to about 90° from axis A.

When sheath 330 is made of a flexible material such as a flexible or semi-rigid plastic, or a flexible shape-memory alloy, angle φ will diminish when sheath 330 is constrained within an endoscope channel. When sheath 330 is extended through an endoscope channel, angle φ will increase as distal end portion 340 of sheath 330 emerges from the distal end of the endoscope channel. Sheath 330 is preferably made of a nickel-titanium shape-memory alloy such as nitinol.

In device 30, sheath 330 defines a lumen 332 and an opening 350 spaced from handpiece 320. Fitting 360 including port 370 forms a liquid and gas-tight seal around sheath 330 and is positioned around sheath 330 such that port 370 is in open communication with opening 350 of sheath 330. Luer lock 380 is secured to port 370 so that luer lock 380 and port 370 are in open communication with the lumen 332 of sheath 330.

As shown in FIG. 5, flared distal end portion 340 of sheath 330 is beveled so that the open end 342 of sheath 330 is roughly parallel to axis A of handpiece 320. Button 390 on handpiece 320 is positioned to indicate the direction of the bend of sheath 330.

Figure 6:
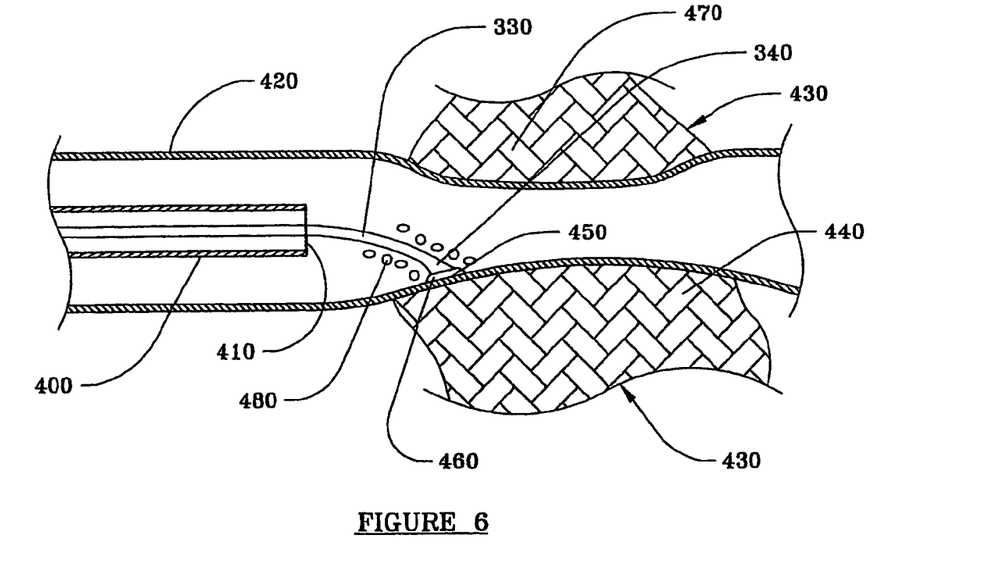
FIG. 6 is a partial external view of the device of FIG. 5, positioned within the male urethra for the treatment of a urinary blockage due to an enlarged prostate.

FIG. 6 illustrates sheath 330 of device 30 (FIG. 5) positioned for use in the treatment of a urethral restriction due to an enlarged prostate. Sheath 330 extends through channel 410 of endoscope 400. Endoscope 400 is positioned within the male urethra 420, just proximal to prostate 430. Flared distal end portion 340 of sheath 330 is positioned to contact the inner surface of urethra 430 over lobe 440 of prostate 430. The flared distal end portion 340 of sheath 330 is beveled at an angle, as described above. The bevel angle of the flare is selected to complement the angle of the bend in sheath 330, enabling the flared distal end portion 340 of sheath 330 to efficiently contact the inner surface of urethra 420 at contact zone 450.

In use, a biocompatible gas, such as air, nitrogen, helium, argon, carbon dioxide, or mixtures thereof is infused through sheath 330 to displace surrounding liquid and create gas bubble 460 within and around the contact zone 450. Excess gas bubbles 480 are shown escaping from main gas bubble 460. The gas bubble 460 displaces fluid from the contact zone 450, creating a fluid-free region through which LW laser light energy can pass with relatively little loss. Light energy from a LW laser can then be emitted from the distal end portion 340 of sheath 330 through laser energy conduit 310 (not shown) positioned within sheath 330 as described above. Very little gas is required to displace the fluid at contact zone 450, and excess gas bubbles 480 escape from gas bubble 460 at contact zone 450 and can be absorbed by the surrounding fluid.

Clearance of fluid from contact zone 450 allows the LW laser energy to efficiently ablate or vaporize tissue from the underlying lobe 440 of prostate 430. Flared distal end portion 340 of sheath 330 can be moved along lobe 440 or 470, and gas can be infused as LW laser energy is emitted. Alternatively, when sufficient tissue has been removed from contact zone 450 by laser irradiation, the flared distal end portion 340 of sheath 330 can be repositioned to form another contact zone 450 with lobe 440 or lobe 470 of prostate 430, and gas can be infused and LW laser energy again can be applied to the tissue as needed, to clear the urethral restriction within the prostate 430.

Figure 7:
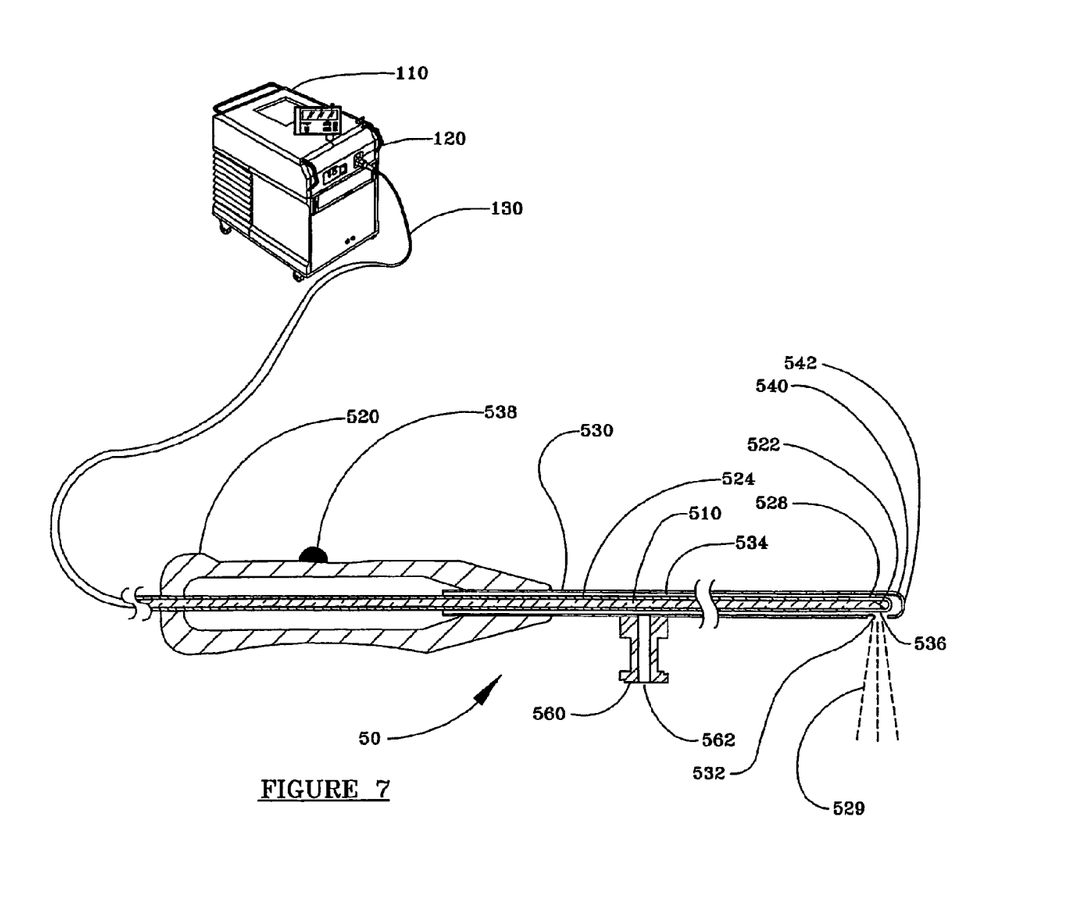
FIG. 7 shows an alternate embodiment of the present invention, partly in section.

FIG. 7 illustrates another embodiment of the present invention. Device 50 is similar to device 20 shown in FIG. 4, except that instead of delivering laser energy forwardly, the distal end surface 522 of optical fiber 510, which extends from the source of laser energy 110 through handpiece 520 and sheath 530, has been beveled at an angle of about 35° to 45°, preferably about 38° to 42°, into a prism-like shape and laser energy is delivered from one side of the device via laser energy port 532 in the sidewall of sheath 530 at the distal end portion thereof.

Plastic cladding and buffer coat 524 encloses and protects optical fiber 510. Plastic cladding and buffer coating 524 preferably are made of vinyl and a polyfluorocarbon (Teflon®), respectively, but may be made of a variety of other materials, as known in the art. In this embodiment, plastic cladding and buffer coat 524 have been removed from the distal end portion of optical fiber 510, and the bared end portion of optical fiber 510 is encased within quartz or fused silica capillary tube 528.

The proximal end of capillary tube 528 is fixedly attached about the proximal bared portion of optical fiber 510 by thermal fusing or an adhesive, as known in the art. Capillary tube 528 creates an air environment (which has a refractive index of 1) about the prism-like, beveled distal end face 522 of a quartz or fused silica optical fiber 510 (which has a refractive index of 1.46). The higher refractive index of the quartz or fused silica fiber is necessary for total internal reflection of light energy. In water, whose refractive index is 1.33, the difference in refractive indexes is not sufficient to cause this effect.

Sheath 530 extends from the distal end of handpiece 520 over optical fiber 510 and terminates in rounded or blunt end portion 542, which may alternatively be made into a sharp point or a syringe-like shape for ease of penetration of tissue. Side port 532 in sheath 530, opposite the laser emitting, beveled end surface 522 of optical fiber 510, permits the laser energy conveyed to beveled end surface 552 to exit sheath 530 laterally, at an angle of about 70° to 90°, from the longitudinal axis of the device as shown by dotted lines 529.

A biocompatible gas, such as carbon dioxide, concurrently infused through luer port 562 of luer fitting 560 into sheath 530, flows through channel 534 and exits through port 532, displacing aqueous irrigation liquid that surrounds the tissue to be vaporized, blood and bodily liquids from the region between the laser emitting surface 526 of capillary tube 528 and the tissue to be affected, reduction or elimination of the loss of laser energy is achieved, which reduction or loss would otherwise occur in vaporizing the intervening liquid, increasing the tissue ablation efficiency of the device. Button 538 on the side of handpiece 520 opposite the direction of emission of laser energy energizes laser source 110 and indicates visually and tacitly to the operator the direction in which laser energy will be emitted when button 538 is depressed.

A layer or coating of reflective material 540 extends over about 30° to 280°, preferably about 60° to 240°, of the back or non-laser energy emitting surface of capillary tube 528 and reflects stray laser energy and laser energy back-scattered from the target tissue back out through side port 532 in sheath 530. Reflective material 540 can be gold, silver, copper, a dielectric or other material which efficiently reflects the wavelength of laser energy being used. For reflecting laser energy at wavelengths of 800 to 1200 nanometers, gold is preferred. Silver is preferred for reflecting laser energy at wavelengths of 1800 to 2200 nanometers, as it is about as efficient in reflecting such wavelengths of laser energy as gold and is less expensive.

Figure 8:
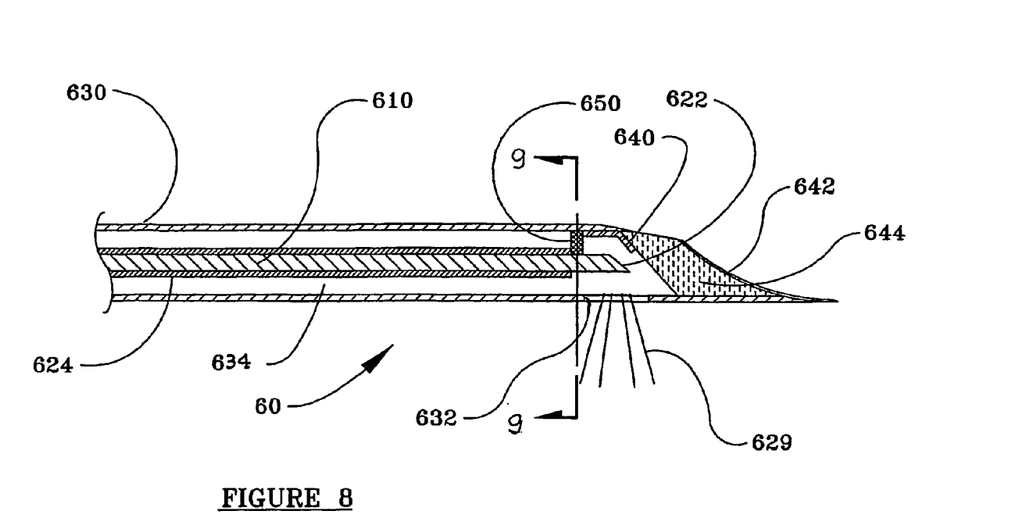
FIG. 8 is an enlarged section view of the distal end portion of a device embodying the present invention.

As shown in FIG. 8, device 60 utilizes optical fiber 610, from whose distal end portion buffer coating and vinyl cladding 624 have been removed. The distal end surface 622 of optical fiber 610 has been beveled at an angle of 35° to 50° preferably about 38° to 42° into a prism-like shape. Optical fiber 610 is held centered within of sheath 630 by spacers 650, 652 and 654, as shown in more detail in FIG. 9. In this embodiment, the distal end 642 of sheath 630 is made into a syringe-like shape to facilitate tissue penetration. The distal end of sheath 630 is closed with plug 644 of an adhesive or other material, as known in the art, to prevent tissue from entering the distal end of sheath 630. The distal end 642 of sheath 630 can also be made into a sharp point or a blunt or rounded shape. A layer of reflective material 640 reflects stray energy outwardly via side port 632.

No capillary tube is needed to maintain an air environment about beveled end surface 622 of optical fiber 610, if a biocompatible gas, such as carbon dioxide, is continuously infused through space 634 between the exterior of optical fiber 610 and the interior of sheath 630. The gas flows over beveled distal end surface 622 of optical fiber 610, creating a gas envelope thereabout, as well as displacing any aqueous liquids from the space between the laser energy emitting surface of optical fiber 610 and the target tissue. The emitted laser energy exits via side port 632.

Figure 9:
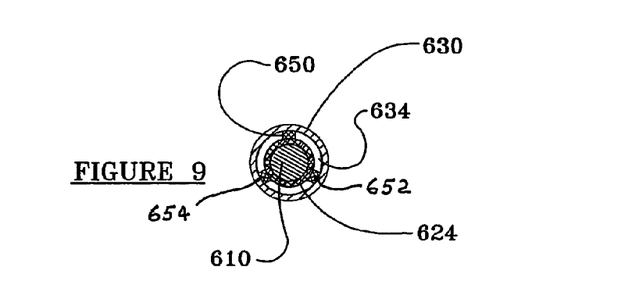
FIG. 9 is a sectional view taken along plane 9-9 in FIG. 8.

FIG. 9 is a cross-sectional, end view of device 60 of FIG. 8 taken at plane 9-9. As shown, three spacers 650, 652 and 654 hold optical fiber 610 within the center of sheath 630, but allow space for a gas to flow over the distal, beveled end surface 622 of optical fiber 610 and out side port 632 of sheath 630. In addition to creating a gas environment about beveled surface 522 of optical fiber 610, a gas stream passing out of side port 632 of sheath 630 displaces aqueous irrigation liquid, blood and other bodily liquids from the space between the laser energy emitting surface of optical fiber 610 and the target tissue, avoiding or at least minimizing the loss of energy and ablative efficiency that would occur if such a gas was not infused through space 634.

Figure 10:
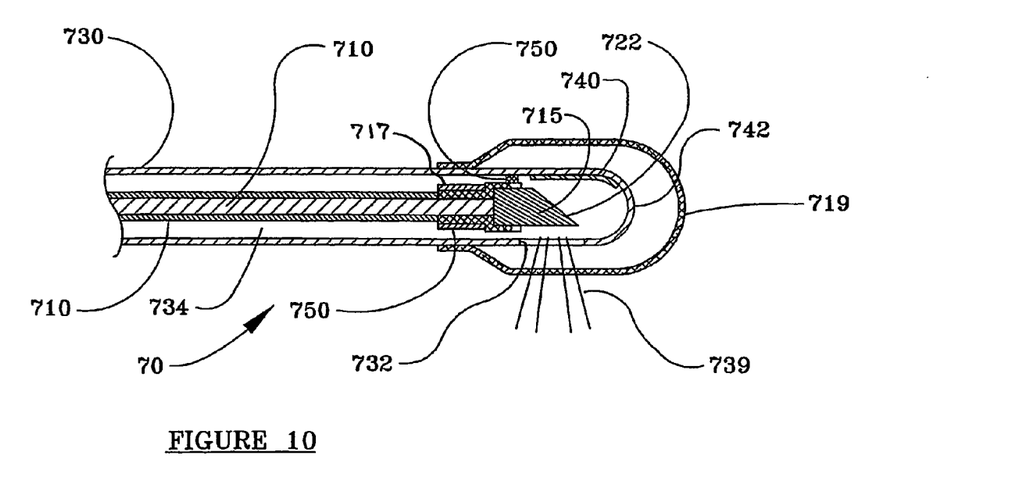
FIG. 10 shows in section yet another distal end portion of a device embodying the present invention.

As illustrated in FIG. 10, device 70 includes sheath 730 with closed distal end 742 and optical fiber 710, opposite whose distal end a short section of light transmissive material 715 is positioned. Light transmission material 715 preferably has an index of refraction significantly higher than water or saline (which have a refractive index of 1.33). Preferred materials include, for example, synthetic sapphire (which has a refractive index of about 1.745) and silica doped with metal oxides, such as SFL-57, made by Schott Glass Technologies, Inc. Duryea, Pa. (which has a refractive index of about 1.811). Reflective layer 740 on the inside of sheath 730 reflects stray layer energy toward side port 732.

The use of such high-refractive index materials is described in co-owned U.S. Pat. No. 5,496,309, which is incorporated herein by reference to the extent pertinent. Material 715 may be held in place opposite the distal end of optical fiber 710 by band or sleeve 717, which may be made of a heat-shrinkable plastic or a plastic or metal fitting sized to accommodate the distal end of optical fiber 710 and the proximal end of material 715, which may be fixed therein by an adhesive or crimping or both. The distal end surface 722 of material 715 is beveled at an angle of about 35° to 50°, preferably about 38° to 42°, creating a prism-like shape.

When a gas, such as carbon dioxide, is continuously infused through space 734 between the exterior of optical fiber 710 and the interior of sheath 730 and flows over material 715 and out of side port 732 of sheath 730, it displaces aqueous irrigation liquid, blood and other body liquids from the space between the laser energy emitting surface of material 715 and the target tissue, thereby minimizing the loss of ablative efficiency that would otherwise occur. Since the refractive index of one of the preferred materials 715 described above is significantly higher than that of water or saline, a gas environment about beveled distal end surface 722 of material 715 is not required to achieve total internal reflection. However, such a device functions more efficiently in a gas environment than in water or saline, due to the lower refractive index of the gas.

As shown in FIG. 10, an optional balloon 719 is disposed over the distal end portion of sheath 730 and occludes side port 732. The distal end 742 of sheath 730 is rounded or blunt. Balloon 719 may be fixedly attached to the exterior of sheath 730 by an adhesive, by friction, or by other means known in the art. Alternatively, balloon 719 may be removeably attached to the exterior of sheath 730 by a tacky adhesive and the like. Balloon 719 is made of material which is transmissive of or transparent to the wavelength of laser energy to be used.

When a biocompatible gas is infused through space 734 between the exterior of optical fiber 710 and the interior of sheath 730 and flows over material 715 and out of side port 732 in the distal end portion of sheath 730, it inflates balloon 719. When balloon 719 of device 70 is brought into contact with the target tissue and inflated, balloon 719, in turn, displaces aqueous irrigation liquid, blood and other bodily liquids from the space between the balloon and the target tissue. The laser energy conveyed by optical fiber 710 passes through balloon 719 to the target tissue and, since the intervening aqueous liquids have been displaced, substantially no loss of laser energy occurs.

Balloon 719 can be removed from the device after each use, thus device 70 can be sterilized and a new, sterile balloon can be attached to the exterior of sheath 730. In this manner device 70 can be reused, reducing cost to the user.

Also, when inflated, balloon 719 spaces device 70 a specific distance away from the target tissue, allowing the laser energy beam to diverge and affect a greater area of the target tissue in a more uniform manner. Balloon 719 may also be employed with device 50 of FIG. 7 or device 60 of FIG. 8 (provided its distal end is rounded or blunt) to achieve the same objectives.

The devices illustrated in FIGS. 7 and 10 can, for example, be inserted through an endoscope into the male urethra to vaporize excess tissue of an enlarged prostate gland to treat benign prostatic hyperplasia (BPH) or into the female uterus to coagulate the endometrial lining of the uterus to treat excessive bleeding, a procedure called endometrial ablation. The device of FIG. 8 can, for example, be introduced into the lobes of an enlarged prostate gland to interstitially vaporize excess tissue, without damaging, except for the puncture, the sensitive urethra. Such a device can also be introduced, for example, into a solid tumor and rotated while emitting laser energy like a beacon to coagulate or vaporize the tumor.

The devices and methods of the present invention can be utilized through an endoscope in a liquid medium to rapidly vaporize, ablate, resect or coagulate tumor tissue or non-malignant fibroid tissue in the female uterus, coagulate the surface of the uterus to treat menorrhagia, or to vaporize or coagulate tumor tissue elsewhere in the body, including the kidney, stomach or other organ. Using a device of the present invention LW laser light energy can effectively coagulate bleeding vessels at a lower level of laser energy than conventional laser devices, enabling the devices of the present invention to be used, after the vaporization or resection procedure, to coagulate or cauterize any remaining bleeding vessels. Lower energy laser energy can also be used to shrink tissues, for example, the nucleus pulposa or annulus of a spinal disc.

The present invention also provides a method of delivering relatively long wavelength laser energy to a body tissue in an aqueous liquid medium. The method involves positioning a laser energy delivery device of the present invention in a body lumen or cavity such as the made urethra, the female uterine cavity, a blood vessel, or a surgically pre-pared channel. The device is positioned so that the distal end of the device is in contact with a tissue site to be irradiated with laser energy. A gas supply source, operably linked to the gas inlet port provides a stream of biologically compatible gas through the lumen of the device sheath, which exits the lumen at its open distal end in contact with the tissue. The gas is supplied at a pressure and flow rate sufficient to displace the aqueous fluid medium surrounding the tissue site at the point of contact with the distal end of the sheath and maintain a substantially liquid-free zone between the distal end of the laser energy conduit component of the device and the tissue to be treated.

In a preferred embodiment, the method comprises the steps of:

(a) providing an endoscope defining at least one channel having an open distal end and an open proximal end;

(b) providing a source of long wavelength laser energy, a laser energy delivery device of the present invention operably coupled to the source of laser energy, and a source of biocompatible gas operably connected to the laser energy delivery device;

(c) positioning the endoscope within a body tissue lumen or cavity such that the open distal end of the endoscope channel is disposed opposite or near a tissue site in need of laser energy treatment;

(d) positioning the laser energy delivery device through the endoscope channel such that the distal end of the device extends through the open distal end of the endoscope channel and contacts a body tissue site in need of laser energy treatment;

(e) supplying gas from the source of biocompatible gas through the laser energy delivery device to the tissue site at a pressure and flow rate sufficient to displace liquid from the tissue site in contact with the open distal end of the sheath and maintain a substantially liquid-free region between the distal end of the laser energy conduit and the body tissue; and (f) supplying long wavelength laser energy from the laser energy source through the substantially liquid-free region to the tissue for a period of time and at a laser energy intensity sufficient to treat the tissue.

The devices of the present invention can be used for treatments such as to effectively fragment or vaporize stones in the urinary tract (a procedure called lithotripsy), to vaporize bone of the lamina or other extensions of the vertebra to open the foraminal space in the spine and enable a portion of a herniated, ruptured or degenerated spinal disc to be vaporized or, at a lower energy level, to be shrunk, to clear a urethral restriction due to an enlarged prostate, to vaporize or coagulate tumor tissue, to cauterize tissue, and the like.

Sources of laser energy useful in conjunction with the device and method of the present invention include filtered, third harmonic Nd:YAG lasers, emitting at about 1,440 nanometers, Holmium:YAG lasers and the like, emitting at about 2,100 nanometers, Erbium:YAG lasers and the like, emitting at about 2,940 nanometers, carbon monoxide (CO) lasers, emitting at about 6,000 nanometers, and carbon dioxide ($CO_2$) lasers, emitting at about 10,600 nanometers.

A preferred source of laser energy is the 80 watt Omnipulse™ MAX Holmium:YAG laser manufactured by Trimedyne, Inc. of Irvine, Calif. This laser emits light energy at a wavelength of about 2,100 nanometers, in pulses with a duration of about 250 to 350 microseconds, with a repetition rate up to 60 pulses per second. The peak energy output of the Omnipulse™ MAX is up to about 3.5 joules per pulse at a repetition rate of about 23 pulses per second (up to about 7 joules per pulse in the Double Pulse™ mode at a repetition rate of about 11 pulses per second).

Typically, a source of laser energy having a wavelength in the range of about 1,300 to about 2,500 nanometers is optically coupled to a laser energy conduit such as an optical fiber or, through mirrors mounted on an articulated arm, to a hollow waveguide. Ordinary quartz or fused silica optical fibers may be used with Alexandrite lasers, but optical fibers with a low hydroxyl content, called "low OH" optical fibers, such as manufactured by the 3M Company of St. Paul, Minn., must be used with Holmium lasers. Laser energy of wavelengths of in the range of about 2,500 nanometers to about 11,000 nanometers is best delivered through a series of mirrors attached to an articulated arm, to whose distal end a short length of hollow waveguide or an optical fiber of a special composition, such as sapphire, zirconium fluoride ($ZrF_4$), chalcogenide ($As_2S_3$), and the like, is attached.

In one preferred embodiment, to facilitate handling of the optical fiber, the handpiece is disposed about 5 to 40 cm, preferably about 10 to 30 cm, from the distal end of the optical fiber. The sheath extends over the laser energy conduit from within the distal end of the handpiece to the distal end of the laser energy conduit. The sheath can be made wholly of metal or plastic or may consist of a metal shaft with an attached soft plastic distal end, a semi-rigid plastic shaft with an attached soft plastic distal end, or a semi-rigid plastic shaft with an attached metal distal end.

The gas inlet port in the sheath or handpiece enables carbon dioxide or other biologically compatible gas to be infused through the space between the exterior of the optical fiber and the interior of the sheath. The sheath can have an inside diameter larger than the outside diameter of the optical fiber, the distal end portion of the sheath may have a somewhat larger diameter than its shaft, or the distal end portion of the sheath can be flared-out into a bell or funnel-like shape.

Flaring-out the distal end of the sheath reduces the risk of the light energy inadvertently striking and burning the distal end of the sheath and creates a reservoir of gas at its distal end. The flared-out end portion of the sheath can be about 0.3 to 2 cm in length, preferably about 0.5 to 1.5 cm long, and can have an inside diameter in the range of about 1.5 to about 5 times the outside diameter of the optical fiber, preferably about 2 to about 3 times the outside diameter of the optical fiber.

The proximal end of the laser energy conduit of a device of the present invention is optically coupled to an appropriate laser energy source. The energy transmitted from the laser source through the energy conduit, such as an optical fiber or hollow waveguide, can be used, for example, to vaporize or resect (cut into sections) an enlarged prostate gland that is blocking urine flow through the urethra, or to vaporize bone to open the foraminal space in the spine.

Typically, for treatment of enlarged prostate, an endoscope is inserted into the urethra through the penis and the distal end of the endoscope is positioned near the prostate. A liquid, such as sterile water, saline, a glucose or dextrose solution, or other clear liquid is infused into the urethra through the distal end of the endoscope. Alternatively, the clear liquid can be simultaneously infused and withdrawn (circulated) to carry away debris and maintain a clear field of view at the distal end of the endoscope. The sheath and optical fiber portion of the device of the present invention is extended through a channel in the endoscope, such that the distal ends of the optical fiber and the sheath project outwardly from the open distal end of the endoscope channel and the distal end of the sheath contacts the tissue to be irradiated.

A biocompatible gas, such as carbon dioxide, is infused through the gas inlet port and into the lumen of the sheath. A gas bubble at the open distal end of the sheath creates a gas "cavity" between the tissue that is to be irradiated and the distal end of the optical fiber. Light energy from the laser is emitted from the distal end of an optical fiber, passes through the gas cavity and into the tissue, where the long wavelength laser energy vaporizes or ablates the tissue. The gas bubble at the distal end of the sheath prevents the aqueous liquid around the tissue from absorbing laser energy being emitted from the optical fiber. It has been found that the use of a gas bubble enhances tissue vaporization by laser energy up to 1.9 times as compared to vaporization without a gas bubble.

In vitro testing, a device constructed as described herein and shown in FIG. 5 was used to vaporize tissue submerged in a water bath. When Holmium:YAG laser energy at a wavelength of 2.1 microns was applied (24,000 Joules over 5 minute period), the vaporization rate was 1.4 to 1.9 times greater with nitrogen gas concurrently infused through the device than without infusing the gas, using the same amount of energy for the same period of time in both cases. The experimental data is shown in Table I, below.

TABLE I

| TISSUE TYPE | ABLATION RATE (grams/min.) | | INCREASE IN ABLATION RATE | % INCREASE |
|---|---|---|---|---|
| | No Gas flow | Gas flow | | |
| Chicken | 0.519 | 0.910 | 0.391 | 75.3 |
| Veal | 1.059 | 1.520 | 0.461 | 43.5 |
| Pig Prostate | 0.409 | 0.750 | 0.341 | 83.4 |

Laser: Omnipulse™ MAX @ 80 watts, 26 Hertz, 3.077 J/pulse
Duration: 5 minutes
Irrigation water: 1.2 ml/minute during lasing Numerous variations and modifications of the embodiments described above can be effected without departing from the spirit and scope of the novel features of the invention. No limitation with respect to the specific apparatus illustrated herein is intended or should be inferred. The appended claims are intended to cover all such modifications as fall within the scope of the claims.

I claim:

1. A laser energy delivery device suitable for delivery of relatively long wavelength laser energy to a biological tissue in an aqueous medium comprising:
   (a) an elongate hollow sheath having an open aperture at distal end portion thereof and a closed proximal end, the sheath defining a lumen and a gas inlet port spaced from the proximal end of the sheath and in open communication with the lumen; and
   (b) a laser energy conduit having a proximal end adapted for connection to a laser energy source capable of generating light having a wavelength of at least about 1,300 nanometers and a distal end adapted for delivery of laser energy emitted from the energy source to a tissue site;
   the laser energy conduit being disposed within the lumen of the sheath and passing through the closed proximal end of the sheath; the distal end of the laser energy conduit being positioned at the open distal end of the sheath; and the gas inlet port being adapted for connection to a gas delivery source for concomitant infusion of a biologically compatible gas through the lumen and the open aperture at distal end portion of the sheath while laser energy is emitted from the distal end portion of the laser energy conduit.

2. The laser energy delivery device in accordance with claim 1 wherein the long wavelength laser energy comprises laser light having a wavelength in the range of about 1,300 nanometers to about 11,000 nanometers.

3. The laser energy delivery device in accordance with claim 1 wherein the laser energy conduit comprises an optical fiber.

4. The laser energy delivery device in accordance with claim 3 wherein the optical fiber is a low-OH optical fiber capable of delivering laser light having a wavelength in the range of about 1,300 nanometers to about 2,500 nanometers.

5. The laser energy delivery device in accordance with claim 1 wherein the laser energy conduit is a wave guide.

6. The laser energy delivery device in accordance with claim 1 wherein the open aperture is substantially coaxial with the laser energy conduit.

7. The laser energy delivery device in accordance with claim 1 wherein the open aperture is offset from the longitudinal axis of the laser energy conduit.

8. The laser energy delivery device in accordance with claim 1 wherein the open aperture is situated at the distal end of the hollow sheath.

9. The laser energy delivery device in accordance with claim 1 wherein the open aperture is situated in a sidewall of the hollow sheath.

10. The laser energy delivery device in accordance with claim 1 wherein the open aperture is occluded with a balloon.

11. The laser energy delivery device in accordance with claim 1 wherein the open aperture is situated at the distal end of the hollow sheath and is occluded with a balloon.

12. The laser energy delivery device in accordance with claim 1 wherein the open aperture is offset from the distal end of the sheath and is occluded with a balloon.

13. The laser energy delivery device in accordance with claim 1 wherein the proximal end of the sheath is provided with a handpiece; and the laser energy conduit extends through the handpiece.

14. The laser energy delivery device in accordance with claim 13 wherein the gas inlet port is spaced from the handpiece.

15. The laser energy delivery device in accordance with claim 13 wherein the gas inlet port is defined by the handpiece.

16. The laser energy delivery device in accordance with claim 15 wherein the gas inlet port includes a valve.

17. The laser energy delivery device in accordance with claim 16 wherein the valve is a needle valve.

18. The laser energy delivery device in accordance with claim 15 wherein the sheath includes a distal end portion having an inside diameter larger than the inside diameter of the remainder of the sheath.

19. The laser energy delivery device in accordance with claim 15 wherein the distal end of the sheath is flared.

20. The laser energy delivery device in accordance with claim 15 wherein the sheath is bent at angle $\phi$ from the axis of the handpiece.

21. The laser energy delivery device in accordance with claim 20 wherein the angle $\phi$ is in the range of about 20 degrees to about 120 degrees.

22. The laser energy delivery device in accordance with claim 20 wherein the angle $\phi$ is in the range of about 30 degrees to about 90 degrees.

23. The laser energy delivery device in accordance with claim 1 wherein the sheath is a stainless steel tube.

24. The laser energy delivery device in accordance with claim 1 wherein the sheath is a semi-rigid plastic tube.

25. The laser energy delivery device in accordance with claim 1 wherein the sheath is a nickel-titanium shape-memory alloy tube.

26. The laser energy delivery device in accordance with claim 1 further comprising a long wavelength laser energy source operably connected to the proximal end of the laser energy conduit.

27. The laser energy delivery device in accordance with claim 26 wherein the long wavelength laser energy source is a Holmium:YAG laser energy source.

28. A method of delivering relatively long wavelength laser energy to a body tissue in an aqueous liquid medium comprising the steps of:
   (a) providing an endoscope defining at least one channel having an inner diameter, the channel having an open distal end and an open proximal end;
   (b) providing a laser energy delivery system which comprises a source of laser energy having a wavelength of at least about 1,300 nanometers;

an elongate hollow sheath defining a lumen, and having an open aperture at distal end portion thereof and a closed proximal end, and further defining a gas inlet port spaced from the closed proximal end of the sheath and in open communication with the lumen, the sheath having an outer diameter smaller than the inner diameter of the endoscope channel and the lumen having an inner diameter;

an elongate laser energy conduit within the lumen of the sheath and extending through the closed proximal end of the lumen, the laser energy conduit having an outer diameter smaller than the inner diameter of the lumen of the sheath, having a proximal end adapted for connection to the source of laser energy and a distal end adapted to emit the laser energy supplied by the laser energy source, the distal end of the laser energy conduit being positioned at the open distal end of the lumen of the sheath; the laser energy source being operably connected to the proximal end of the laser energy conduit; and a source of biocompatible gas operably connected to the gas inlet port;

(c) positioning the endoscope within a body tissue lumen or cavity such that the open distal end of the endoscope channel is disposed generally opposite a tissue site in need of laser energy treatment;

(d) positioning the sheath of the laser energy delivery system through the endoscope channel such that the distal end of the sheath extends through the open distal end of the endoscope channel and contacts a body tissue site in need of laser energy treatment;

(e) supplying gas from the source of biocompatible gas through the gas inlet port and lumen of the sheath to the tissue site, at a pressure and flow rate sufficient to displace fluid from the tissue site in contact with the open distal end of the sheath and maintain a substantially fluid-free region between the distal end of the laser energy conduit and the body tissue; and (f) supplying long wavelength laser energy from the laser energy source through the distal end of the laser energy conduit to the tissue through the substantially liquid-free tissue region for a period of time and at a laser energy intensity sufficient to treat the tissue.

29. The method in accordance with claim 28 wherein the long wavelength laser energy source supplies laser energy having a wavelength in the range of about 1,300 nanometers to about 11,000 nanometers.

30. The method in accordance with claim 28 wherein the laser energy conduit comprises a low-OH optical fiber and the laser energy source supplies laser energy having a wavelength in the range of about 1,300 nanometers to about 2,500 nanometers.

31. The method in accordance with claim 30 wherein the laser energy source is a Holmium:YAG laser energy source.

32. The method in accordance with claim 28 wherein the biocompatible gas is selected from the group consisting of nitrogen, helium, argon, carbon dioxide, air, and a combination thereof.

33. The method in accordance with claim 28 wherein the treatment comprises vaporization or ablation of tissue from the body tissue site.

34. The method in accordance with claim 33 wherein the treatment comprises vaporization or ablation of prostate tissue to relieve or lessen a urethral restriction due to an enlarged prostate.

35. The method in accordance with claim 28 wherein the treatment comprises cauterization of tissue at the body tissue site.

36. The method in accordance with claim 28 wherein the treatment comprises shrinking the tissue at the body tissue site.

* * * * *